(12) United States Patent
Umeda et al.

(10) Patent No.: US 8,044,177 B2
(45) Date of Patent: Oct. 25, 2011

(54) WATER-SOLUBLE KERATIN DERIVATIVE AND USE THEREOF

(75) Inventors: Keiji Umeda, Tokyo (JP); Yositaka Nadachi, Tokyo (JP); Katsunobu Sakai, Hokkaido (JP); Yukitaka Nogami, Chiba (JP); Masahiko Sudo, Saitama (JP)

(73) Assignees: Umeda Jimusho Ltd., Machida-shi (JP); Institute of Rheological Function of Food Co., Ltd., Fukuoka (JP); Asai Germanium Research Institute Co., Ltd., Kawasaki-shi (JP)

( * ) Notice: Subject to any disclaimer, the term of this patent is extended or adjusted under 35 U.S.C. 154(b) by 113 days.

(21) Appl. No.: 12/559,949

(22) Filed: Sep. 15, 2009

(65) Prior Publication Data
US 2010/0069612 A1    Mar. 18, 2010

Related U.S. Application Data

(62) Division of application No. 11/670,190, filed on Feb. 1, 2007, now abandoned, which is a division of application No. 10/522,336, filed as application No. PCT/JP03/09449 on Jul. 25, 2003, now abandoned.

(30) Foreign Application Priority Data

Jul. 25, 2002 (JP) ................................. 2002-215944

(51) Int. Cl.
*C07K 1/12* (2006.01)
*C07K 14/435* (2006.01)
*C09K 9/02* (2006.01)
*C09K 109/00* (2006.01)

(52) U.S. Cl. .................. 530/357; 252/588; 252/193
(58) Field of Classification Search .................. 530/357; 252/588, 193
See application file for complete search history.

(56) References Cited

U.S. PATENT DOCUMENTS

| | | | |
|---|---|---|---|
| 4,279,996 | A | 7/1981 | Yoshioka et al. |
| 6,613,398 | B1 | 9/2003 | Tada et al. |
| 7,169,896 | B2 * | 1/2007 | Schrooyen et al. ........... 530/350 |
| 2002/0108903 | A1 | 8/2002 | Homonoff et al. |

FOREIGN PATENT DOCUMENTS

| | | |
|---|---|---|
| JP | 2-51533 | 2/1990 |
| JP | 4-312534 | 11/1992 |
| JP | 5-320358 | 12/1993 |
| JP | 06-46871 | 2/1994 |
| JP | 7-328390 | 12/1995 |
| JP | 09-118576 | 5/1997 |

(Continued)

OTHER PUBLICATIONS

Harrap, B.S., et al., Soluble Derivatives of Feather Keratin, 1. Isolation, Fractionation and Amino Acid Composition, Biochem. J., vol. 92, No. 1, pp. 8-18 (1964).

(Continued)

*Primary Examiner* — Rosanne Kosson
(74) *Attorney, Agent, or Firm* — Oblon, Spivak, McClelland, Maier & Neustadt, L.L.P.

(57) ABSTRACT

The present invention provides a novel water-soluble keratin derivative and applications thereof. Water-soluble keratin produced by the alkali treatment of feathers, and modified keratin, gives the following useful materials: (1) a high energy wave absorber, (2) a luminescent substrate, (3) a material weatherproofness improver, (4) a water repellant, and (5) a foaming agent.

13 Claims, 19 Drawing Sheets

FOREIGN PATENT DOCUMENTS

| | | |
|---|---|---|
| JP | 9-173301 | 7/1997 |
| JP | 2001-11313 | 1/2001 |
| JP | 2001-322998 | 11/2001 |

OTHER PUBLICATIONS

Harrap, B.S., et al., Soluble Derivatives of Feather Keratin, 2. Molecular Weight and Conformation, Biochem. J., vol. 92, No. 1, pp. 19-26 (1964).

Woodin, "Molecular size, shape and aggregation of soluble feather keratin," Biochem J, vol. 59, pp. 99-109 (1954).

Sigma-Aldrich, on-line catalogue record for Trizma base BioUltra, record No. 93349, http://www.sigmaaldrich.com/catalog/search/ProductDetail/FLUKA/93349, printed from the Internet on Aug. 29, 2008.

Kim, et al., "Effect of enzymatic and chemical treatments on feather solubility and digestability", Poultry Sci, vol. 81, No. 1, pp. 95-98 (Jan. 1, 2002).

Zvia, The Science of Hair Care, C. Zviak, Informa Health Care, London, pp. 185-187 (1986).

* cited by examiner

GRAPH 1

GRAPH 2

GRAPH 3

GRAPH 4

WATER-SOLUBLE KERATIN DERIVATIVE AND USE THEREOF

This is a divisional application of U.S. application Ser. No. 11/670,190, filed Feb. 1, 2007, now abandoned, which is a divisional application of U.S. application Ser. No. 10/522,336, filed Jan. 25, 2005, now abandoned, which is a 371 of PCT/JP03/09449 filed on Jul. 25, 2003.

TECHNICAL FIELD

This invention relates to the creation of a suitable technique for transforming the morphology and characteristics of mass-produced natural protein sources, and to the creation of novel applications arising from a better understanding of novel functionality of such modified proteins.

More particularly, the present invention relates to the development of a technique for transforming the morphology and characteristics of waste feathers from birds, and especially poultry, to the search for functionality of feathers whose morphology and characteristics have been transformed, and to the creation of novel applications thereof.

BACKGROUND ART

There are no official statistics relating to the quantity of poultry feathers produced as by-products in the production of chicken meat and eggs, but if we do a rough calculation based on the internal reference materials one of the world's largest chicken producers, we find that the annual by-product quantity in the US is up to two million tons, and the Japanese by-product quantity extrapolated from this figure would be 150,000 tons.

Both in the US and here in Japan, the majority of the by-product feathers produced at chicken meat production plants is rendered into feather meal along with internal organs and other by-products due to their high collectability, but the majority of the feathers that are the by-product of chicken egg production plants is treated as industrial waste due to their low collectability.

Despite having good supply stability, a high protein value, and low cost, feather meal has been deemed the least valuable protein material for use as feed. The main reason for this is that it is deficient in essential amino acids and difficult for animals to digest.

In view of this situation, recent years have witnessed the development of techniques for transforming the morphology of poultry feathers, aimed mainly at making them finer, and there have been attempts at making use of the inherent water repellency and heat retention (thermal insulation) of feathers. Nevertheless, this presents the dilemma of high finished product price and the inability to create corresponding bulk demand, and so far no one has found a way to overcome this problem.

SUMMARY OF THE INVENTION

It is an object of the present invention to develop a cost-effective technique for transforming the morphology and characteristics of poultry feathers, and thereby create new bulk demand that takes advantage of both the known characteristics and the unknown latent features of feathers.

Analysis of the flight environment of migratory birds, and thought experiments into this environment, have led to the prediction that in addition to their known functions of heat retention (thermal insulation), light weight, waterproofness, and so forth, bird feathers also have an unknown and latent "high energy wave irradiation resistance," and as a result of diligent research conducted with this as the target function, into a technique for transforming the morphology and characteristics of feathers with the aim of realizing this goal, the inventors perfected the present invention upon discovering that this goal could be achieved by subjecting feathers to desulfurization and water solubilization with an alkali, and subjecting this product to a high energy wave irradiation treatment.

The stated object is achieved by technological means of the following steps with the present invention.

(1) The conversion of poultry feathers into a water-soluble keratin derivative by subjecting the feathers to a) an alkali desulfurization and water solubilization reaction step and b) a step of separating the water-soluble main component, or by subjecting the feathers to a) and b) and then c) a high energy wave irradiation step.

(2) The conversion into a water-soluble keratin derivative according to (1) above, wherein the molecular weight is from 5 to 50 kDa.

(3) The conversion into a water-soluble keratin derivative according to (1) or (2) above, wherein the feathers are treated with an aqueous solution containing an alkali with a concentration of at least 1.1% in an amount of at least 2 wt % with respect to the feather weight.

(4) The conversion into a water-soluble keratin derivative according to (1), (2), or (3) above, wherein UV-C is used as the primary source of high energy waves.

(5) A high energy wave absorber containing the water-soluble keratin derivative according to any of (1), (2), (3), and (4) above.

(6) A fluorescent material containing the water-soluble keratin derivative according to any of (1), (2), (3), and (4) above.

(7) A material weatherproofness improver containing the water-soluble keratin derivative according to any of (1), (2), (3), and (4) above.

(8) A water repellant containing the water-soluble keratin derivative according to any of (1), (2), and (3) above.

(9) A rustproofing agent containing the water-soluble keratin derivative according to any of (1), (2), and (3) above.

(10) The high energy wave absorber according to (5) above, wherein the high energy waves are ultraviolet rays or an electron beam.

The raw material in the present invention is bird feathers, and preferably poultry feathers. Examples of poultry include meat broilers, laying hens, domesticated ducks, and wild ducks, with preferred examples including broilers and laying hens.

In addition to poultry feathers, down from waterfowl is a favorable example of feathers here. The poultry feathers that are a by-product in meat and waste chicken processing plants are preferably collected right away while still fresh, rinsed of any foreign matter, finely chopped, compressed and packaged, and then stored in a cool, dark place. Feathers are capable of metal ion adsorption and oil absorption and are readily oxidized, among other properties, so care must be exercised in their handling and processing.

In the alkali water solubilization of the raw material feathers, it is preferable for the feathers to have been finely chopped. After this chopping, the down portion and the quill portion can be separated and then subjected to the alkali treatment separately. The amount in which the raw material feathers are supplied should be within a range that allows the alkali treatment to be carried out reasonably. If the feathers are to be added in a single batch, this amount may be 5 to 20% with respect to the treatment liquid, but this does not apply if the feathers are to be added intermittently. Any alkali may be used as long as it is water-soluble, but caustic soda is preferable. A water-insoluble alkali, such as calcium hydroxide, active clay, or an ion exchange resin, can be used for the purpose of avoiding desalting from the reacted solution.

The alkali treatment conditions should be within a range that does not bring about any abnormal reactions in the keratin that is the main component of the raw material feathers. The required amount of alkali is 2 to 15%, and preferably 4 to 10%, as a weight ratio with respect to the feathers. The reaction temperature may be from room temperature to the temperature at which protein is thermally denatured, such as 80° C. or lower, and preferably 20 to 70° C. The alkali concentration should be within a range that avoids a state of local strong alkalinity, and is from 1.1 to 20%. Because the reaction system is heterogeneous, the reaction method may be one that allows the alkali aqueous solution to come into contact efficiently with the insoluble feathers, and may be either a batch or continuous method. The treatment should last long enough for the feathers to dissolve, as long as it does not take an extremely long time. If needed, the solution can be decolored or deodorized by a standard method.

Upon completion of the treatment, the remaining water-soluble alkali is subjected under cooling to neutralization with a suitable acid, preferably hydrochloric acid, to desalt it and remove the low-molecular weight fraction. If an insoluble alkali is used, it is directly filtered by a standard method. This product is an oligokeratin with a molecular weight of 100,000 or less, and for the purposes of the present invention it is preferable for the molecular weight to be from 5 to 50 kDa.

The neutralized solution and membrane-treated solution are concentrated by a standard method and dried by a suitable method to obtain a "water-soluble keratin derivative I" powder (hereinafter referred to as "MFP").

Meanwhile, an aqueous solution of the above treatment solution in a suitable concentration of 1 to 20%, and preferably 2 to 10%, is put in a specific UV (preferable UV-C) irradiation reactor and reacted for 2 to 100 hours, at a suitable temperature not over 80° C., under stirring, and at a suitable irradiation intensity.

Any by-product low-molecular weight compounds (molecular weight under 10,000, and preferably under 5000) are removed from this UV-irradiated solution as needed with a commercially available membrane. The irradiated solution and the membrane-treated solution are concentrated to a specific concentration by a standard method to obtain a "water-soluble keratin derivative II" aqueous solution (hereinafter referred to as "WP"). Alternatively, a "water-soluble keratin derivative II" powder is prepared by evaporating to dryness a solution of a specific concentration, or subjecting it to spray drying or freeze drying.

The altered/modified feathers thus obtained ("water-soluble keratin derivative I" (MFP) and "water-soluble keratin derivative II" (UVP)) were surmised from the results of various experiments to be oligo-β-keratin derivatives with a molecular weight of several dozen kDa, and to have a multi-heterocyclic structure.

In addition to the targeted high energy wave resistance, this oligo-β-keratin derivative has a wide range of functions, including high energy wave absorption, hydrolysis resistance, protease resistance, amphipatic property, heavy metal scavenging, and so forth.

These various functions should make this derivative useful as a high energy wave absorbent, such as UV protection products (skin care and hair care toiletries, cosmetics, underwear and other apparel, and laundry detergents), and weatherproofness improvers for various kinds of materials (plastic stabilizers, paint additives, ink additives, papermaking additives, and so forth), and because this derivative is amphipatic, it should be useful as additives such as water repellants, rustproofing agents, surfactants, foaming agents, and so on. And, because this derivative has the function of emitting fluorescent light upon absorbing high energy waves, it should be useful as a substrate for various kinds of light emitting materials.

DETAILED DESCRIPTION OF THE INVENTION

The present invention will now be described in specific terms through reference to examples, but the present invention is not limited in any way by the following examples.

Example 1

Manufacture of Water-Soluble Keratin Derivative (MFP))

1 Raw Materials and Pretreatment Thereof

Laying hen feathers that were a by-product in a chicken processing plant were collected immediately from a standard plucking line while still fresh, any foreign matter was removed, the feathers were washed for a suitable time and at a suitable temperature with an ultrasonic washer, in some cases the feathers were then finely chopped, then the water was removed from the feathers and this product was airtightly packaged, then stored in a cool, dark place until use as the raw material.

2 Alkali Treatment of Feathers

1) Alkali Reaction 200 g of de-watered feathers (dry weight: 100 g) were added to 1 kg of a 4% NaOH aqueous solution and stirred at room temperature. After the feathers became downy, the reaction solution was warmed and held at 70° C., and the stirring was continued for about 5 hours until the down and quills had completely dissolved.

2) Treatment of Reaction Solution; Neutralization

Upon completion of the alkali reaction, 1 N hydrochloric acid was added dropwise while the system was cooled, which neutralized the remaining alkali and sulfides. During this time the by-product hydrogen sulfide was trapped in the alkali.

Any hydrogen sulfide still remaining in the reaction solution was completely removed by adding a hydrogen sulfide trapping agent and heating.

3) Filtration of Neutralization Treatment Solution

Suction filtration was performed by a standard method, using Celite as a filtration auxiliary.

4) Desalting and Aliquoting

The filtrate was ultra-filtered as follows, and separated/aliquoted into three fractions with molecular weights of less than 10,000, at least 10,000 but less than 50,000, and at least 50,000, with the respective amount ratio being 2:7:2.

Apparatus used:
- Stirring-type Ultra-Holder UHP-90K, made by Advantech Toyo
- Filters: UK-10 (passes substances with molecular weight of less than 10,000)
- UK-50 (passes substances with molecular weight of less than 50,000)
- Operation: according to the manual 5) Concentration and Drying Each fraction was suitably concentrated with a rotary evaporator, and subjected to freeze drying with a commercially available apparatus. The dry yield of the fraction with a molecular weight of 10,000 to 50,000 was 49 g (yield from raw material of 49%).

6) Measurement of MFP (Molecular Weight of 10,000 to 50,000) Characteristics (1) Measurement of Molecular Weight Distribution; Aqueous GPC Using the following apparatus, the relative molecular weight (kDa) distribution was measured for MFP (prepared with a 10,000 to 50,000 ultrafiltration membrane) versus a reference protein (see below).

Figure 1:
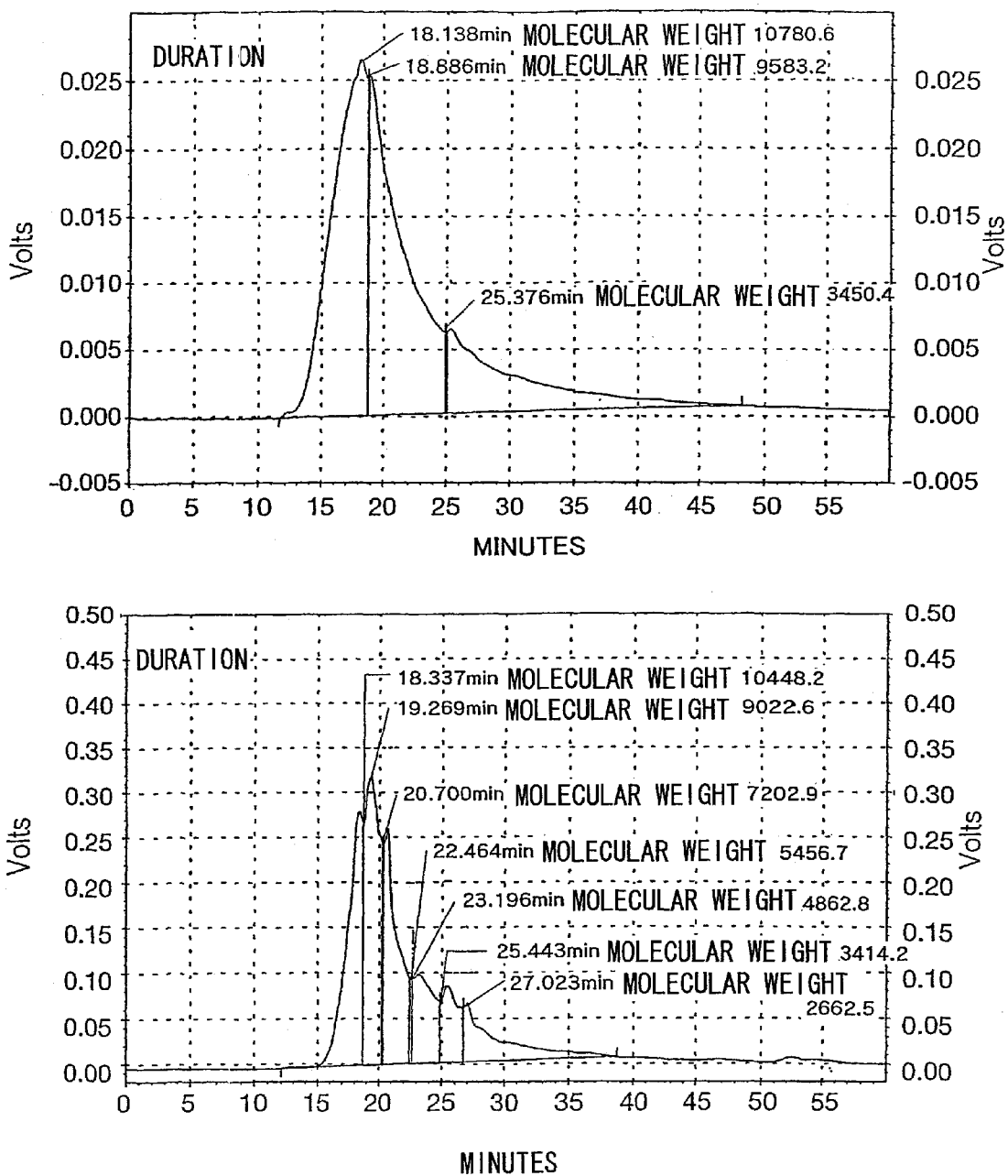
FIG. 1 shows the results of measuring molecular weight distribution.

As a result, main peaks were measured at 9.6 and 10.8 kDa. The chart is given in FIG. 1.

Apparatus
- HPLC unit: CCPM-II made by Tosoh
- Column oven: CO-8020 (30° C.) made by Tosoh
- Detector: SD-8022 made by Tosoh
- Data processor: Vstation Ver. 1.65 made DL Science
- Column: Shodex Asahi Pak GF310 HQ (8 mmφ×300 mm), applicable molecular weight range: up to 50,000
- Reference protein: 5 types of protein with molecular weights ranging from 1350 to 67,000 (Bio-Rad Filtration Standard)

Measurement Conditions
- Buffer: disodium hydrogenphosphate 0.1 m/L
- Buffer pH: 9.04 (unadjusted)
- slow rate: 0.5 mL/min
- Amount of specimen added: 20 μL
- Measurement time: 60 min.

(2) Amino Acid Composition: Measurement Using Automatic Amino Acid Analyzer

A characteristic of the product was that it contained a large amount of lanthionine, which was not contained in the raw material feathers, but was lacking in cystine, which is abundant in feathers. This indicates that lanthionine is being produced through a cystine desulfurization reaction by the alkali. The results are given in Table 1.

TABLE 1

| Amino acid | MFP | Feathers(barbs) |
|---|---|---|
| Lysine | 0.9 | 1.0 |
| Histidine | 0.1 | 0.4 |
| Arginine | 3.8 | 6.5 |

TABLE 1-continued

| Amino acid | MFP | Feathers(barbs) |
|---|---|---|
| Tryptophan | 0.1 | 0.3 |
| Aspartic acid | 6.7 | 6.1 |
| Glutamic acid | 11.9 | 10.1 |
| Serine | 6.8 | 11.4 |
| Threonine | 2.5 | 5.3 |
| Tyrosine | 2.5 | 1.8 |
| Glycine | 7.7 | 5.2 |
| Alanine | 4.5 | 3.6 |
| Valine | 6.4 | 7.2 |
| Isoleucine | 4.1 | 5.0 |
| Leucine | 8.3 | 7.5 |
| Phenylalanine | 5.5 | 5.0 |
| Proline | 10.5 | 11.0 |
| Cystine | 1.2 | 9.6 |
| Methionine | 0.8 | 1.1 |
| Lanthionine | 4.8 | 0 |
| Total | 89.1 | 98.1 |

(3) UV Absorption

The test aqueous solution was put in a specific quartz cell (optical wavelength 1 cm), and its absorption performance was found from the absorption spectrum given by a commercially available UV spectrophotometer. The results are given below. The absorption of various wavelengths is given as the specimen concentration at which 90% of the UV rays were blocked. As a control, bovine serum albumin (crystals) were also measured.

TABLE 2

| UV wavelength | A (365 nm) | B (312 nm) | C (254 nm) |
|---|---|---|---|
| Control (albumin) | 20.8 | 6.2 | 0.4 |
| Concentration (wt/v %) | 1.2 | 0.5 | 0.1 |

Table 3 below shows the results of measuring the UV absorption performance of the low-molecular weight fraction (the fraction that passed through the UK-10 filter mentioned in section 2-4 above).

TABLE 3

| UV wavelength | A (365 nm) | B (312 nm) | C (254 nm) |
|---|---|---|---|
| Control (albumin) | 20.8 | 6.2 | 0.4 |
| Concentration (wt/v %) | 2.3 | 1.0 | 0.15 |

This fraction had main peaks at 10.4 and 9.1 kDa in the aqueous GPO spectrum thereof (lower row in Table 1), indicating that quite a lot of MFP fraction was admixed. Therefore, most of the above-mentioned UV absorption capability of this low-molecular weight fraction was ascribed to the participation of the admixed MFP, leading to the conclusion that a low-molecular weight fraction of 6 kDa or lower has Low UV absorption.

(4) IR Absorption Spectrum

Figure 2:
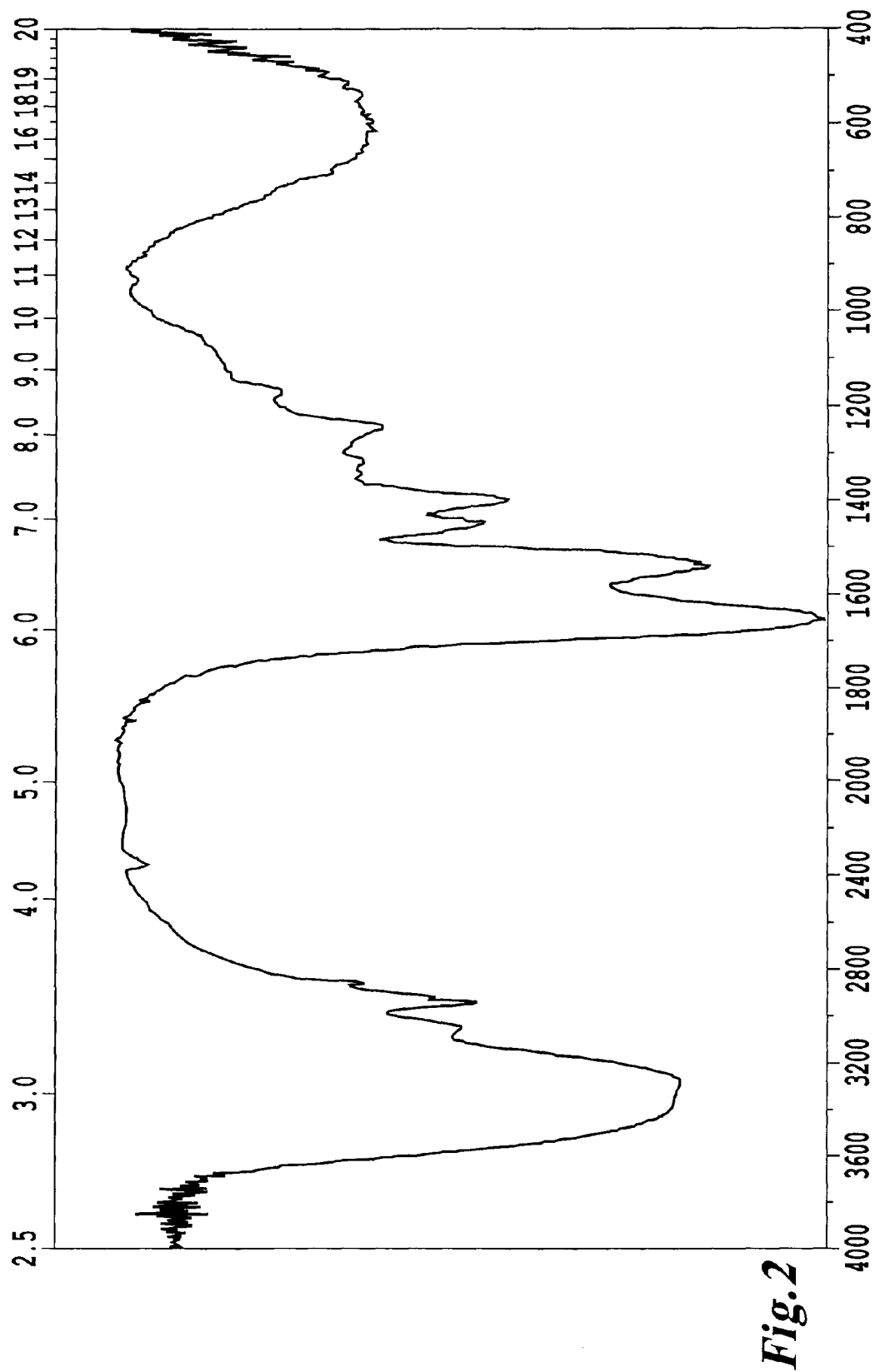
FIG. 2 is an IR chart.

FIG. 2 is an IR chart for a KBr press-molded sample.

(5) Heat Resistance: Differential Thermal Analysis

Figure 3:
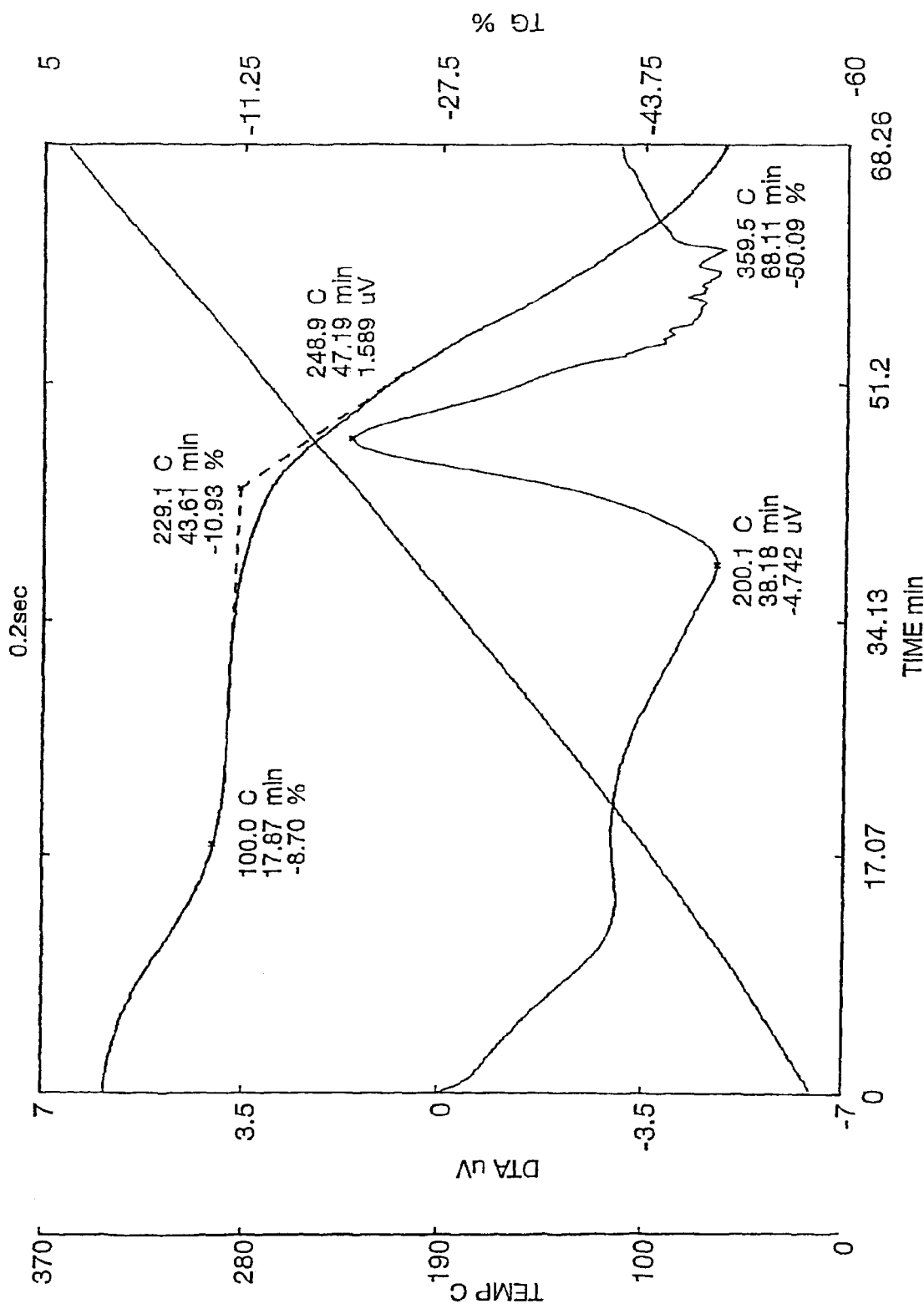
FIG. 3 shows heat resistance characteristics.
Figure 4A:
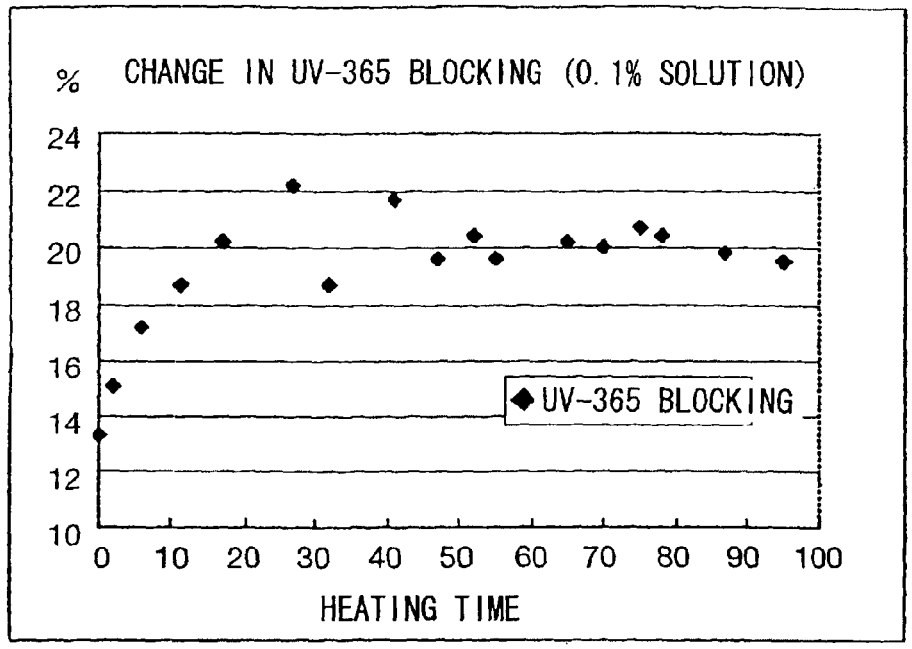
FIGS. 4a and 4b show UV absorption performance.
Figure 4A:
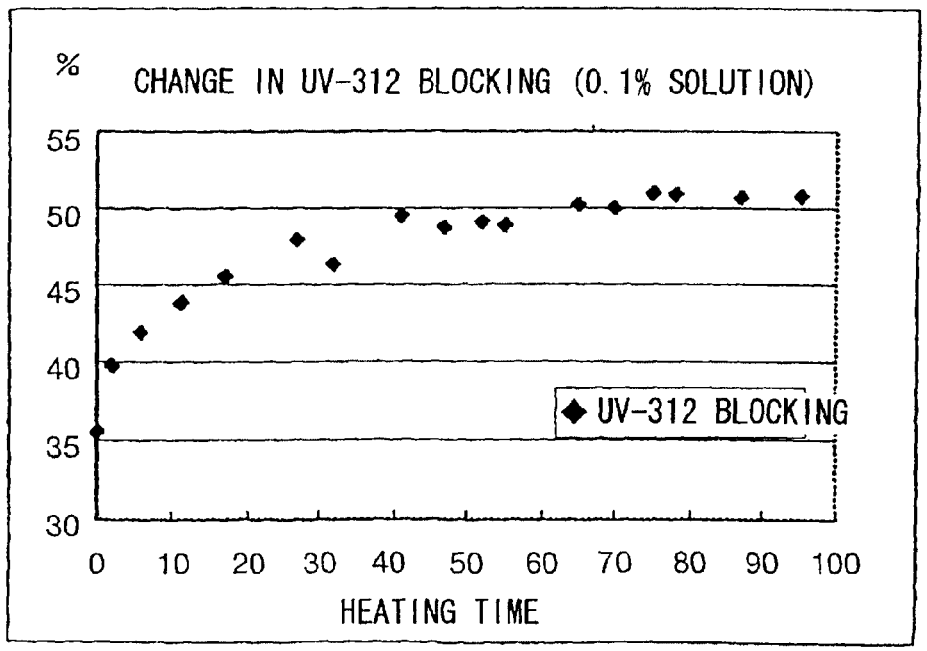
Figure 4B:
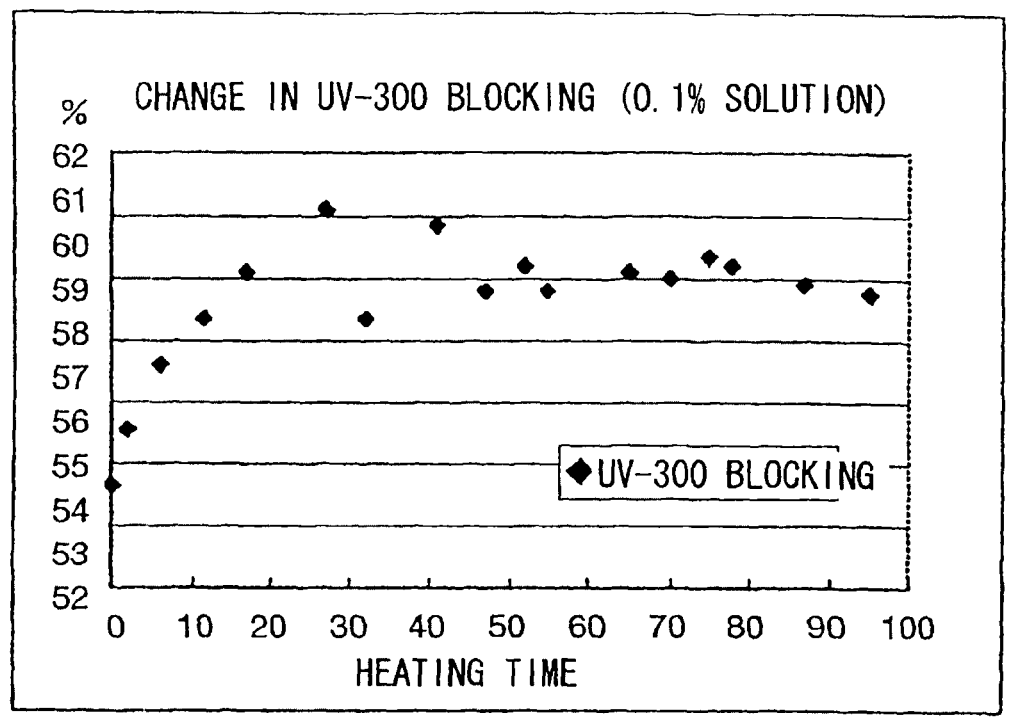
Figure 4B:
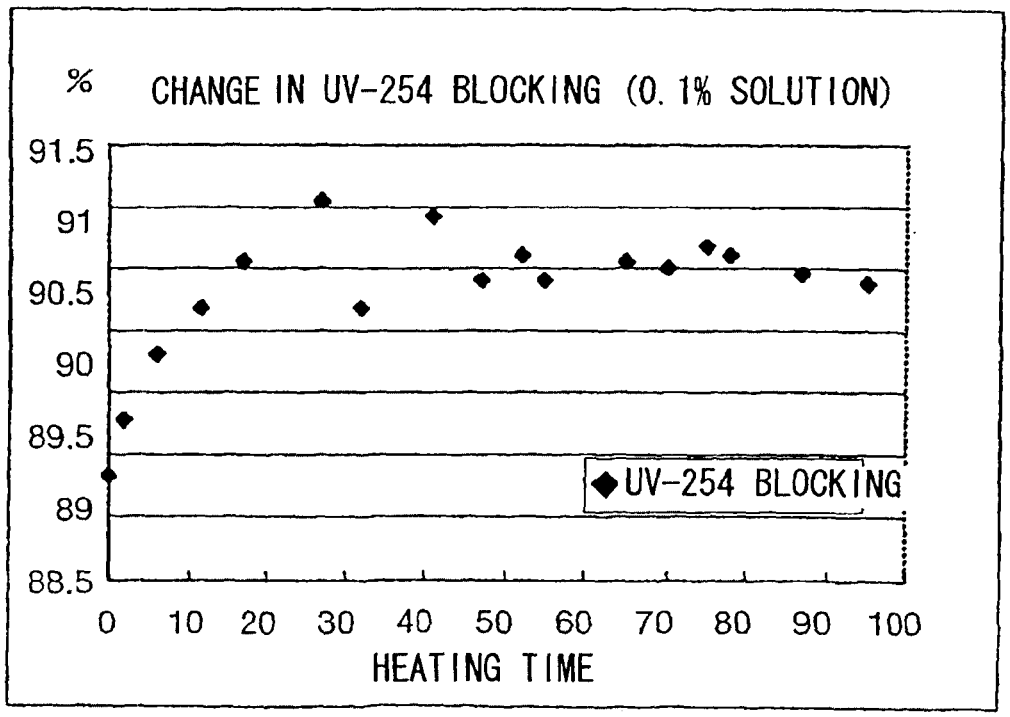

The heat resistance was over 200° C. FIG. 3 shows a chart.

(6) Melting Point/Decomposition Point; Found from Differential Thermal Analysis Chart The raw material feathers exhibited a melting point of 200° C. and a decomposition temperature of 229° C. versus a melting point of 235° C. and a decomposition temperature of 275° C.

(7) Dissolution Characteristics

MFP dissolved extremely well in water. It also dissolved slightly in oil (neutral vegetable oil), making it amphipatic.

(8) Alkali Resistance

Figure 5:
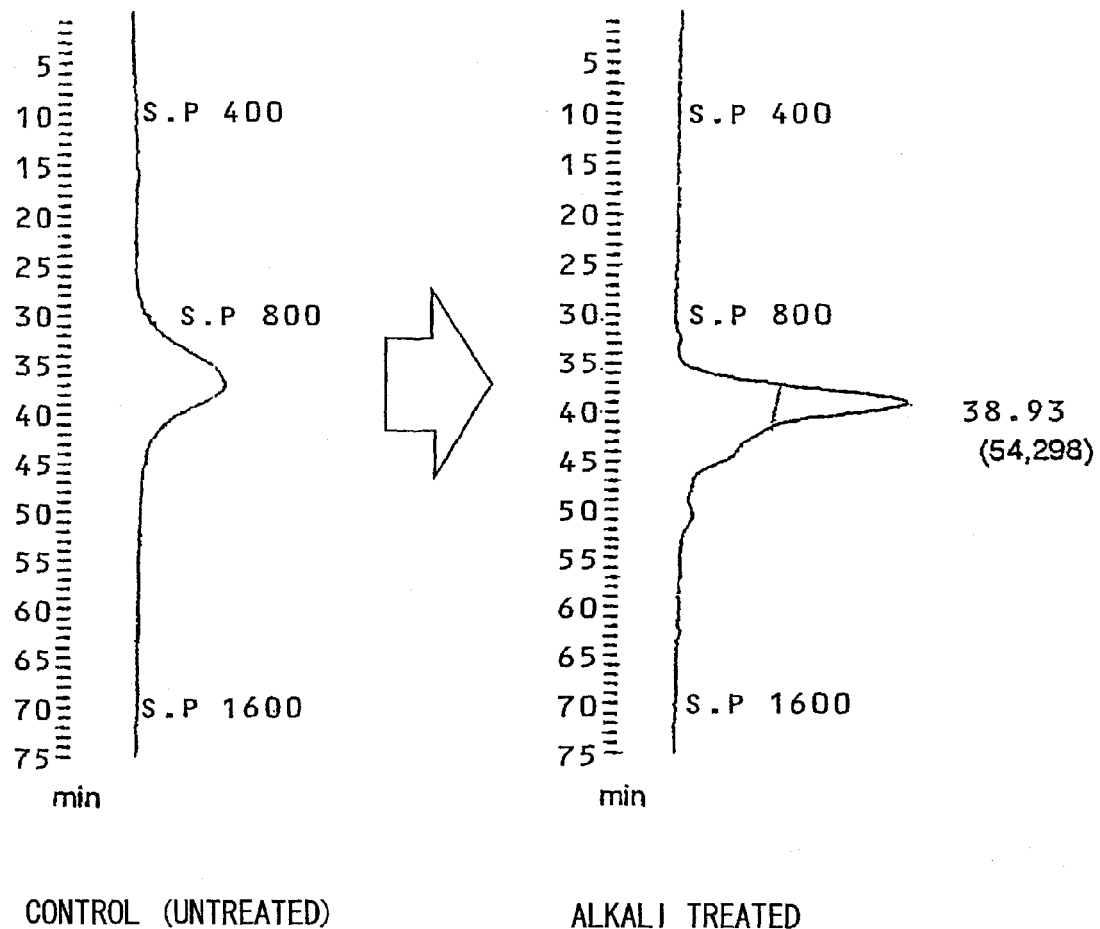
FIG. 5 shows HPLC spectra.

A 10% 1 N NaOH aqueous solution of MFP powder was heated for 95 hours at 70° C., but there was no decrease whatsoever in the UV-A, -B, or -C absorption performance, nor was any major change noted in the HPLC spectrum. FIG. 4 shows the absorption performance, while FIG. 5 is a chart.

HPLC Measurement Conditions
Main apparatus: Hitachi HPLC System:
    Pump: L-6200
    Detector: UV-VIS L-4250
Column: Superdex 200 HR 10/30 (Pharmacia)
Measurement Conditions:
    Flow rate: 0.5 mL/min
    Pressure: 7 kg/cm$^2$
    Eluant: PBS (+)
    Absorption wavelength: 280 nm
    Amount added: 5 μL (=5 μg) of 0.1% aqueous solution of MFP
    Temperature: room temperature (9) UV Irradiation Resistance An MFP dilute aqueous solution was irradiated with UV rays for 24 hours at room temperature, and its stability was evaluated.

With UV-A and UV-B, there was no change whatsoever in the UV absorption, so stability was extremely high. A peculiar phenomenon was observed with UV-C irradiation, however. Specifically, no major change that would suggest decomposition was seen at all in the HPLC spectrum, and in terms of UV absorption performance, this performance generally increased, and the increase was particularly great at longer wavelengths.

Figure 6:
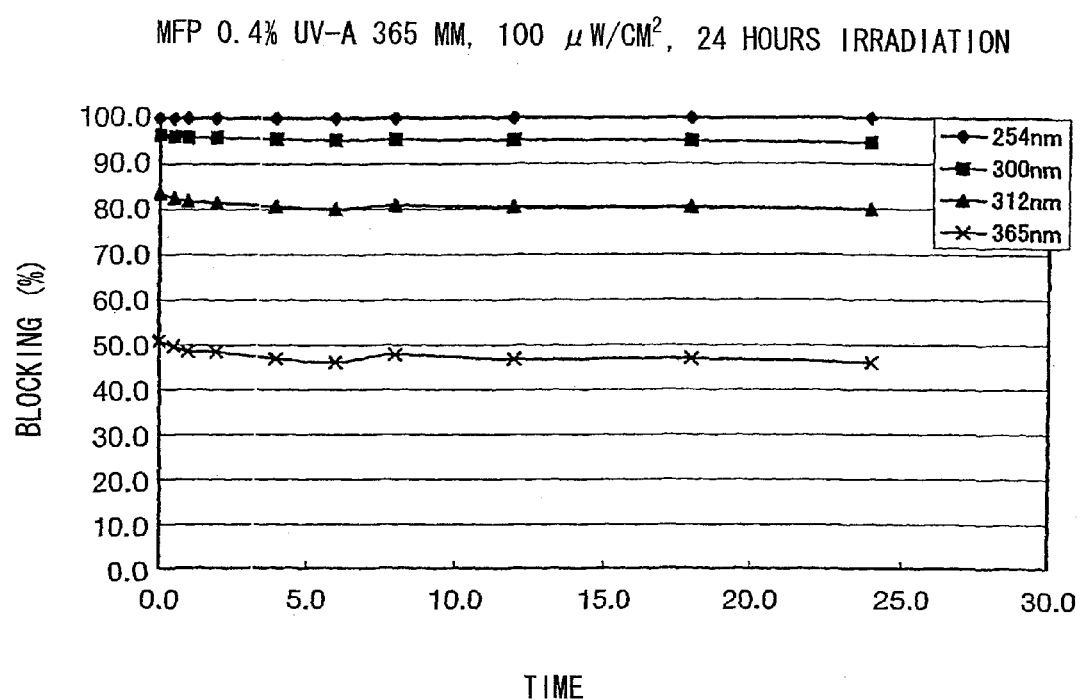
FIG. 6 shows the results of UV-A irradiation.
Figure 7:
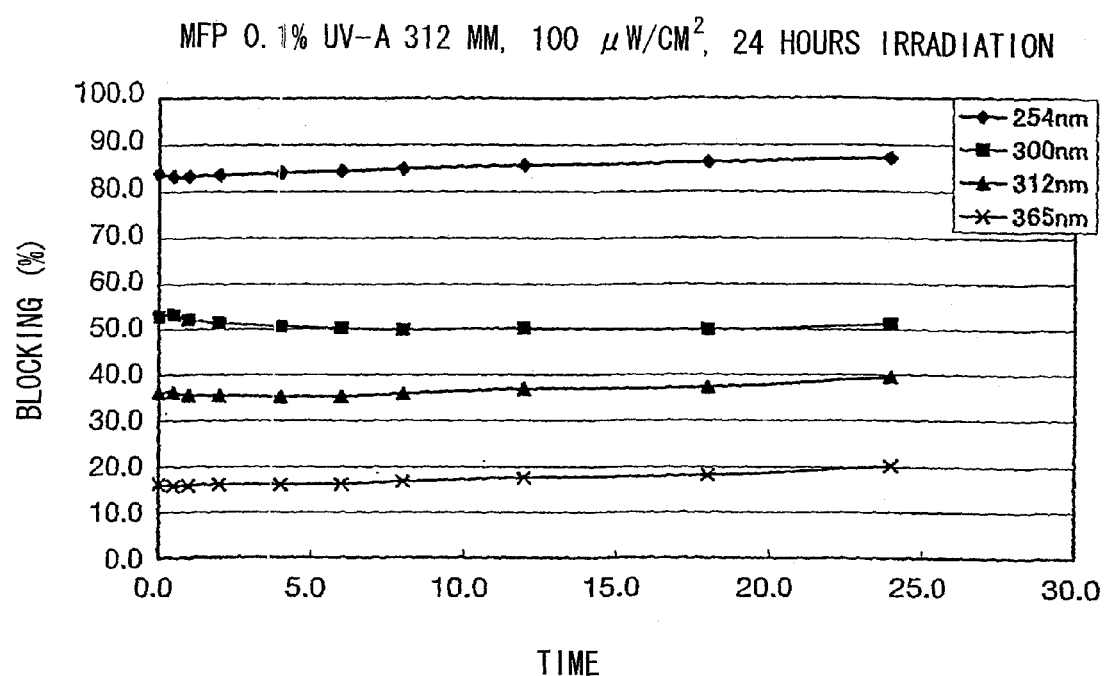
FIG. 7 shows the results of UV-B irradiation.
Figure 8:
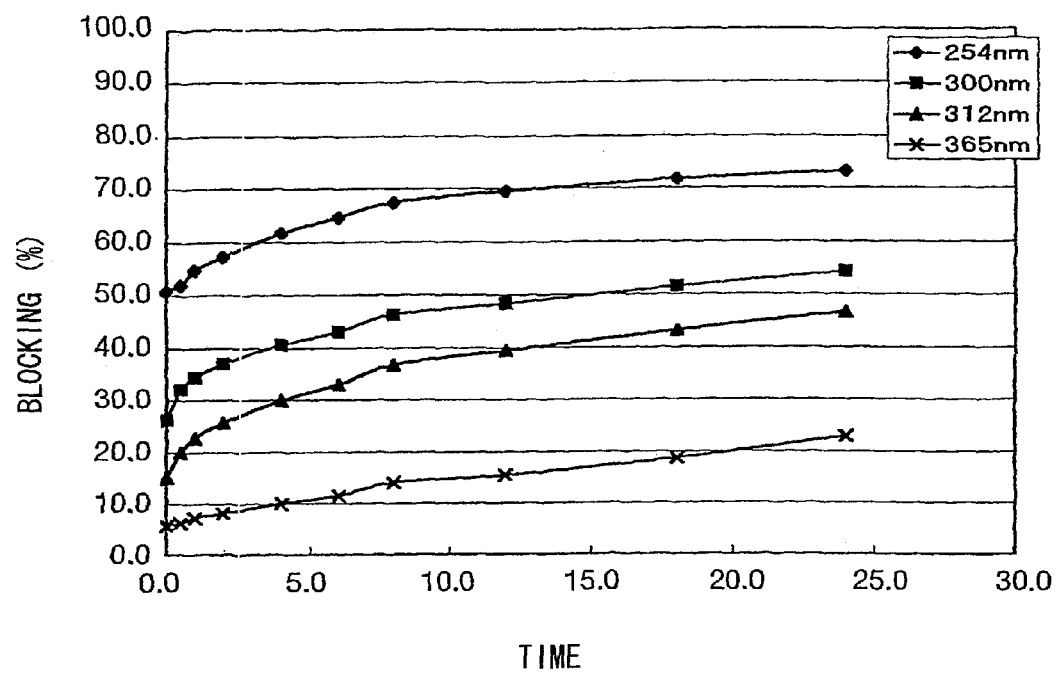
FIG. 8 shows the results of UV-C irradiation.

FIGS. 6, 7, and 8 show the results of irradiating with UV-A, UV-B, and UV-C, respectively.

(10) Electron Beam Irradiation Response

An MFP powder coated surface was irradiated with a 2.0 kV electron beam using an electron microscope made by JEOL, and the light emission from the surface was observed. As a result, an extremely broad range of emission was seen extending all the way to 600 nm and having a maximum at 430 nm.

Figure 9:
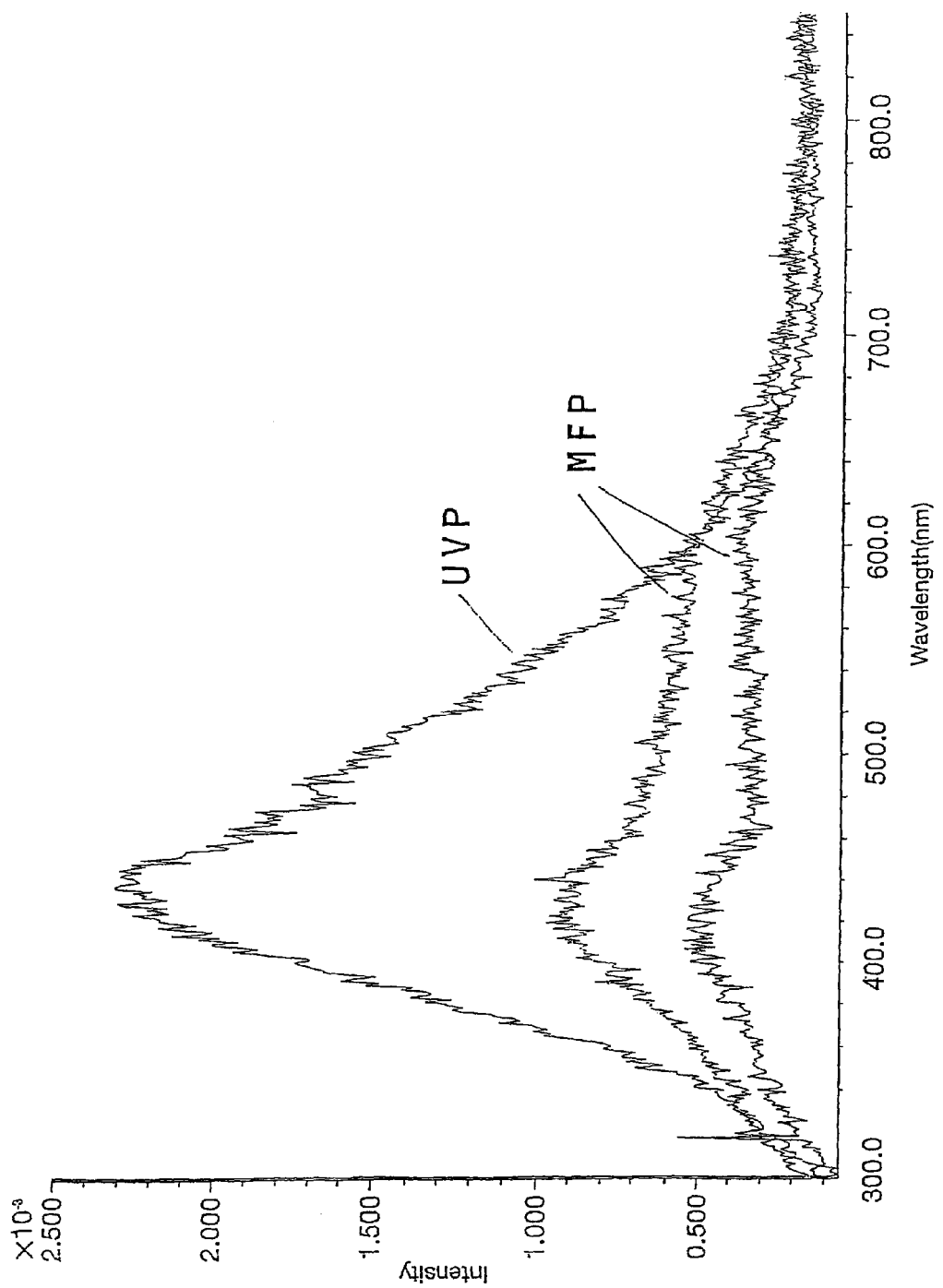
FIG. 9 shows electron beam irradiation response.

FIG. 9 shows a chart of this. This indicates that MFP has a cathode luminescence function.

Example 2

Preparation of UVP by UV-C Irradiation of MFP Aqueous Solution

1) UV-C Irradiation Reaction

An alkali reaction solution was desalted and subjected to ultrafiltration to filter off the fraction with a molecular weight below 10,000. This filtrate was adjusted to a solids concentration of 2% and charged into the following UV-C irradiation reaction apparatus, where it underwent a photochemical reaction for 60 hours at room temperature while heat was removed.

UV ray irradiation lamp:
    Cold cathode sterilizing lamp QCGL-5W (made by Iwasaki Electric)
    Wavelength: UV-C 80% (including 20% 180 nm)
    Irradiation intensity:
        35 μW/cm$^2$; 5 cm
        800 μW/cm$^2$; 1 cm Reaction apparatus: A UV lamp was directly inserted into a glass beaker containing the reaction solution, and the solution was stirred with a magnetic stirrer. The beaker was externally cooled.

2) Treatment of Post-Reaction Solution

Following Celite filtration, concentration and freeze drying were carried out by a standard method to obtain a water-soluble keratin derivative II (UVP) powder at a yield of 84%.

3) Measurement of UVP Characteristics (1) Molecular Weight Distribution

Figure 10:
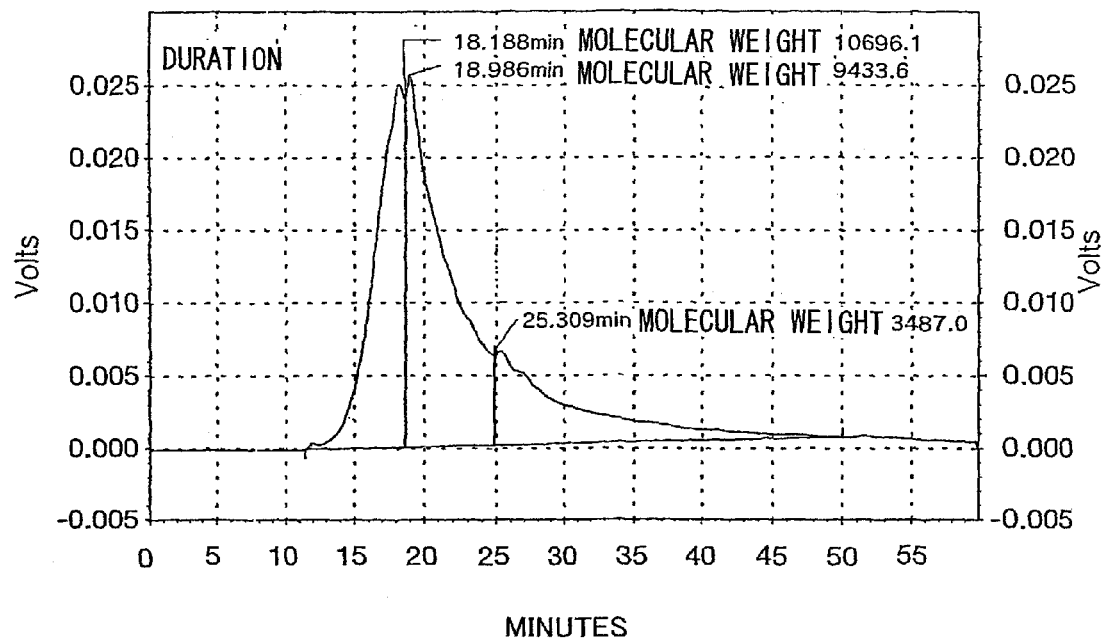
FIG. 10 shows molecular weight distribution.

FIG. 10 shows the aqueous GPC spectrum. It can be seen that UVP exhibits a molecular weight distribution pattern similar to that of the raw material MFP. The measurement apparatus and conditions were the same as discussed above.

(2) Amino Acid Composition

This composition is shown in Table 4, and is similar to that of the raw material MFP.

TABLE 4

| Amino acid | UVP | Feathers(barbs) |
|---|---|---|
| Lysine | 0.6 | 1.0 |
| Histidine | 0.1 | 0.4 |
| Arginine | 3.1 | 6.5 |
| Tryptophan | 0.1 | 0.3 |
| Asparatic acid | 6.5 | 6.1 |
| Glutamic acid | 11.1 | 10.1 |
| Serine | 6.6 | 11.4 |
| Threonine | 2.4 | 5.3 |
| Tyrosine | 2.0 | 1.8 |
| Glycine | 7.7 | 5.2 |
| Alanine | 4.1 | 3.6 |
| Valine | 6.0 | 7.2 |
| Isoleucine | 4.0 | 5.0 |
| Leucine | 8.3 | 7.5 |
| Phenylalanine | 5.5 | 5.0 |
| Proline | 10.0 | 11.0 |
| Cystine | 0.3 | 9.6 |
| Methionine | 0.5 | 1.1 |
| Lanthionine | 5.3 | 0 |
| Total | 84.2 | 98.1 |

(3) UV Absorption: The measurement method was the same as in section 6) of Example 1.

TABLE 5

| UV wavelength | A (365 nm) | B (312 nm) | C (254 nm) |
|---|---|---|---|
| Control (MFP) | 1.2 | 0.5 | 0.1 |
| Concentration (wt/v %) | 0.38 | 0.17 | 0.08 |

UV-A, UV-B, and UV-C absorption was improved, and the increase was particularly pronounced in the absorption of A and B, which are useful in practical applications.

(4) IR Absorption Spectrum

Figure 11:
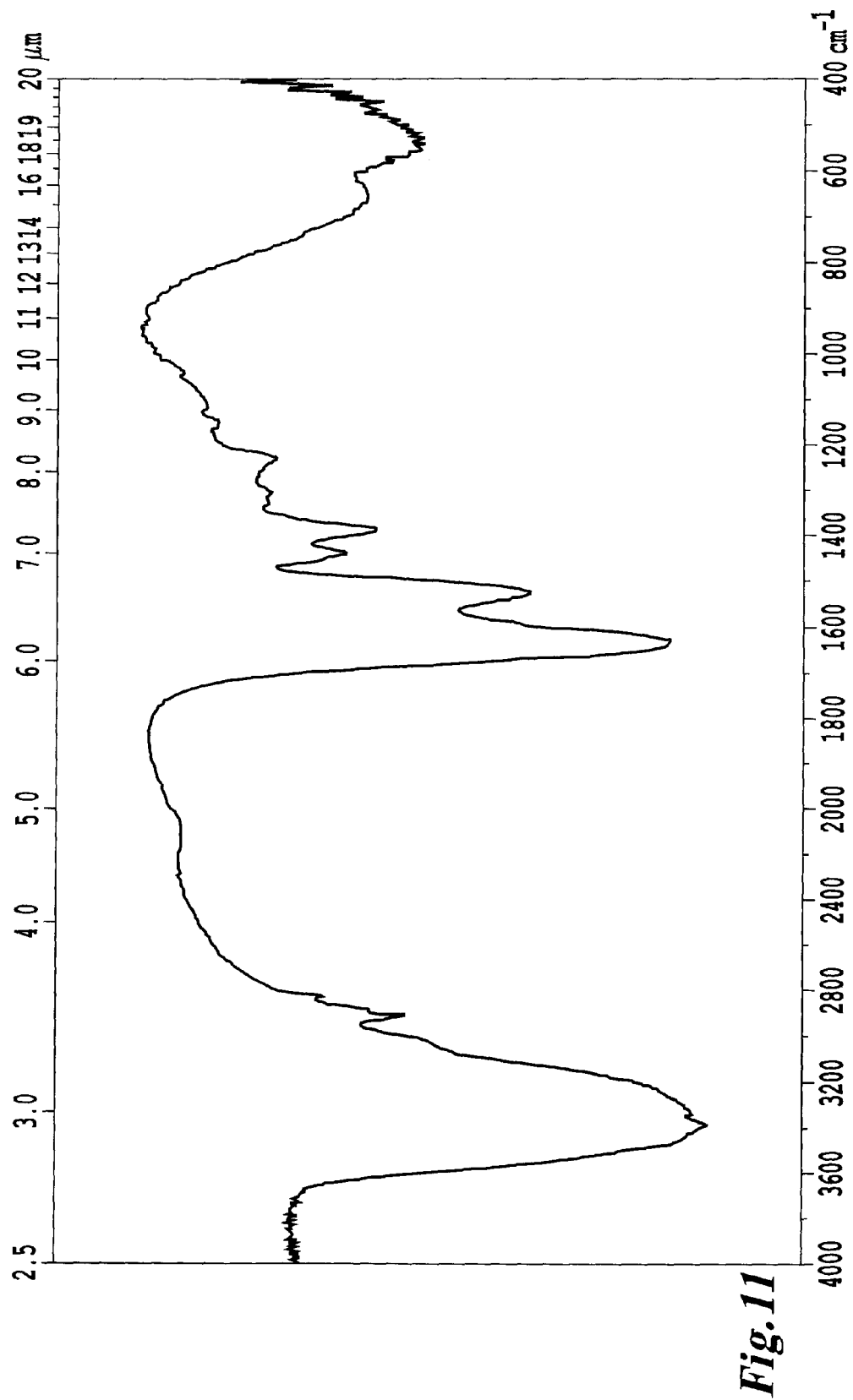
FIG. 11 shows IR absorption spectrum.

This is shown in FIG. 11. The obtained spectrum was similar to that of the raw material MFP.

Figure 12:
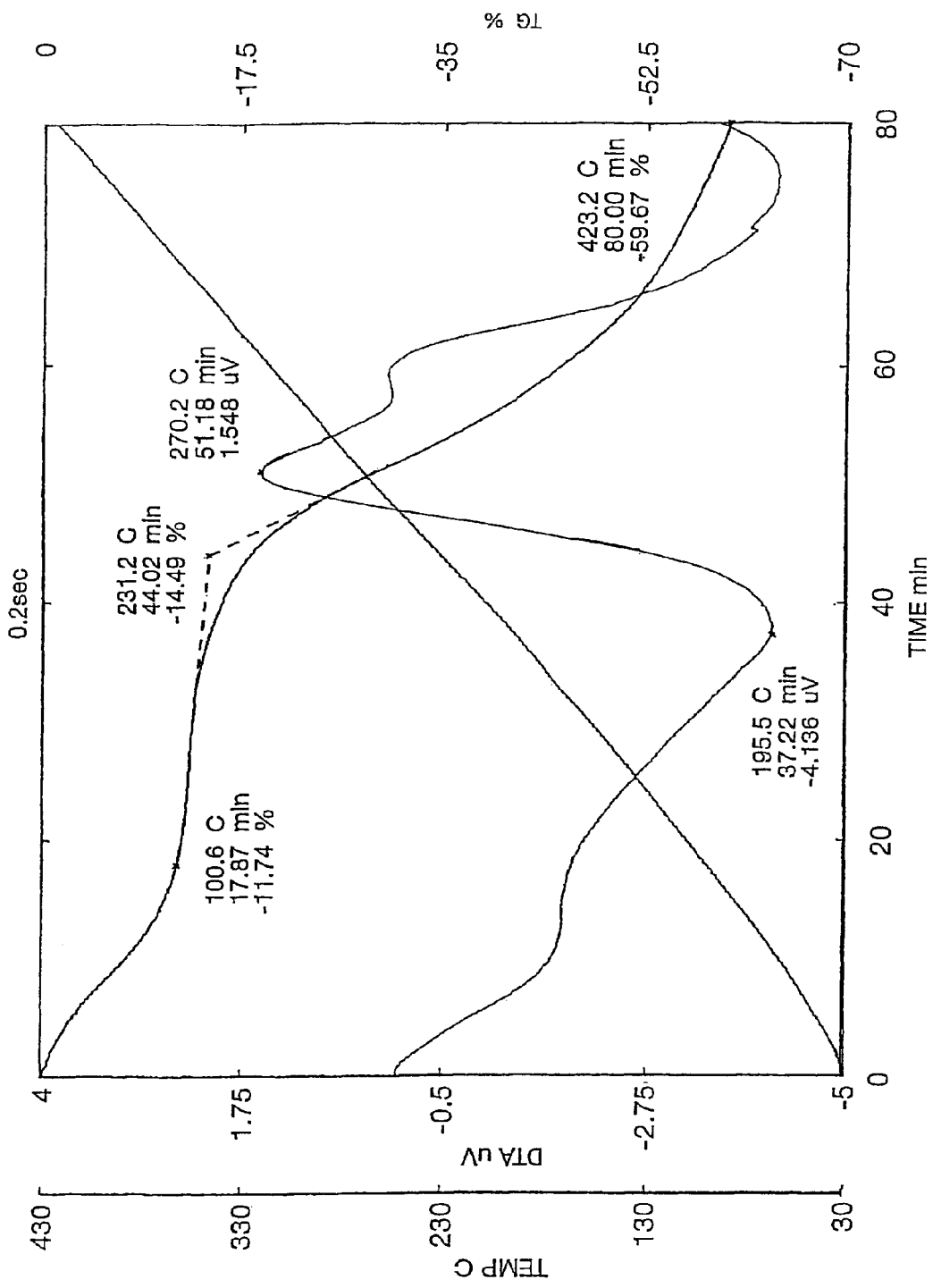
FIG. 12 is a differential thermal analysis chart.

(5) Heat resistance: FIG. 12 shows the differential thermal analysis chart. The UVP exhibited heat resistance on a par with that of MFP.

(6) Melting Point/Decomposition Point

From a differential thermal chart, the melting point was 195° C. and the decomposition temperature was 231° C.

(7) Dissolution Characteristics

UVP dissolved extremely well in water, and also dissolved slightly in oil, making it amphipatic.

(8) Protease Resistance

Figure 13A:
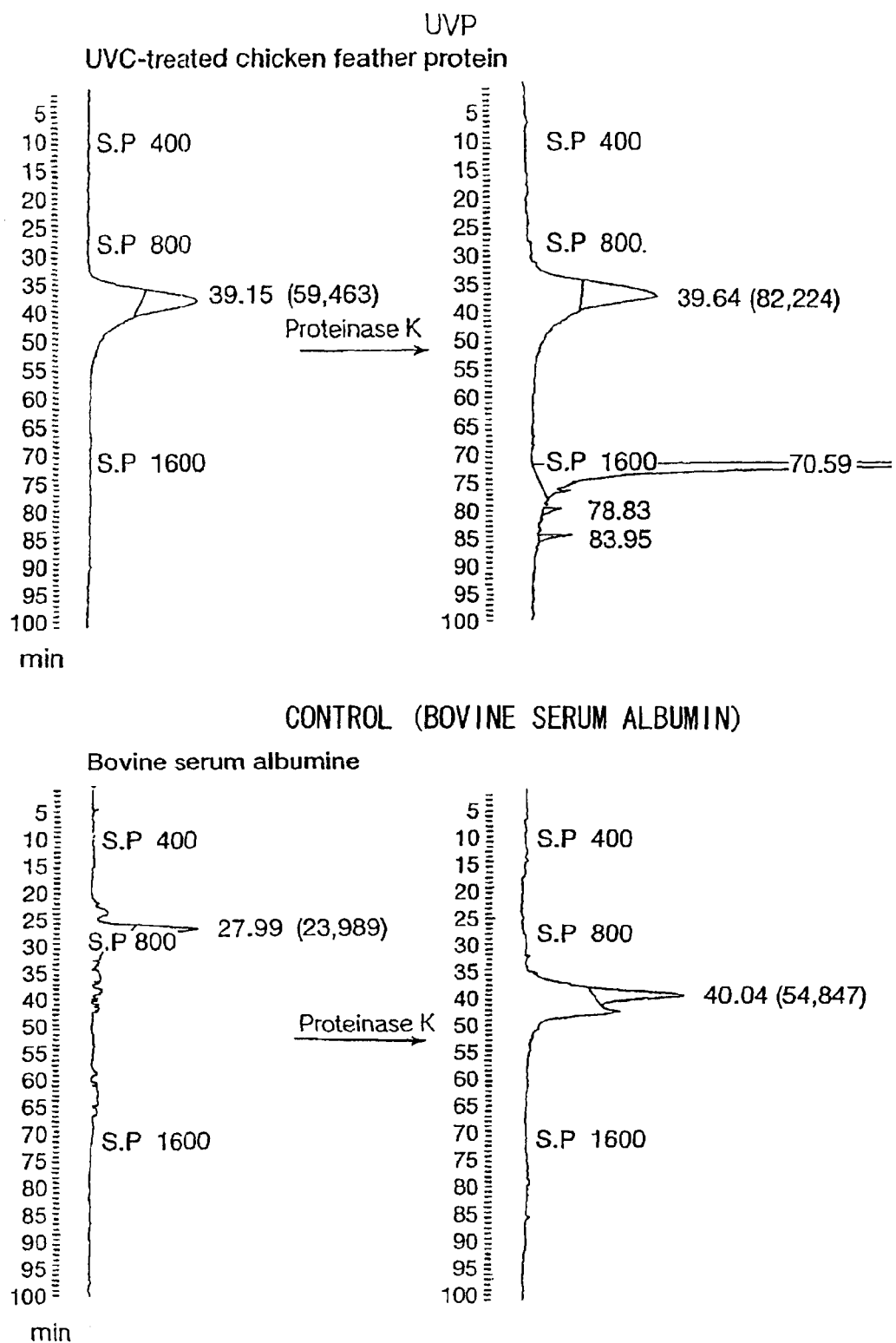
FIGS. 13a and 13b are HPLC charts.
Figure 13B:
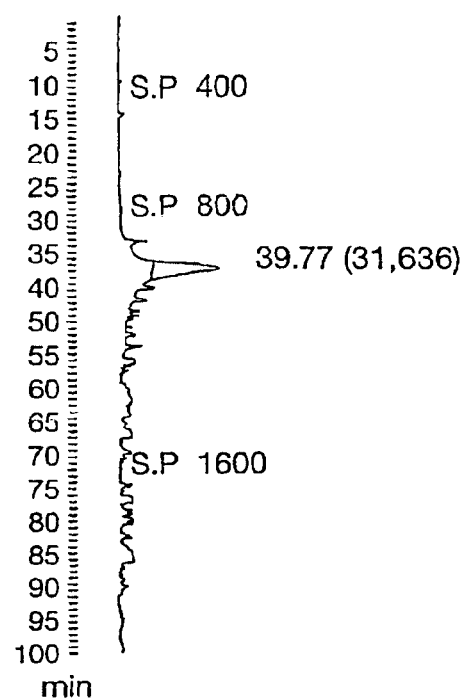

10 μL of 1 M CaCl$_2$ and 6 mU of proteinase K were added to UVP 1 mg/mL 10 mM tris-HCl (pH 7.5), and a powerful digestion reaction was conducted for 90 minutes at 37° C. Upon completion of the reaction, the solution was subjected to HPLC under the following conditions, which gave the chart in FIG. 13.

This chart suggests that the basic skeletal structure of UVP does not become the substrate of protease. The bovine serum albumin used as a control was completely digested.

Figure 14:
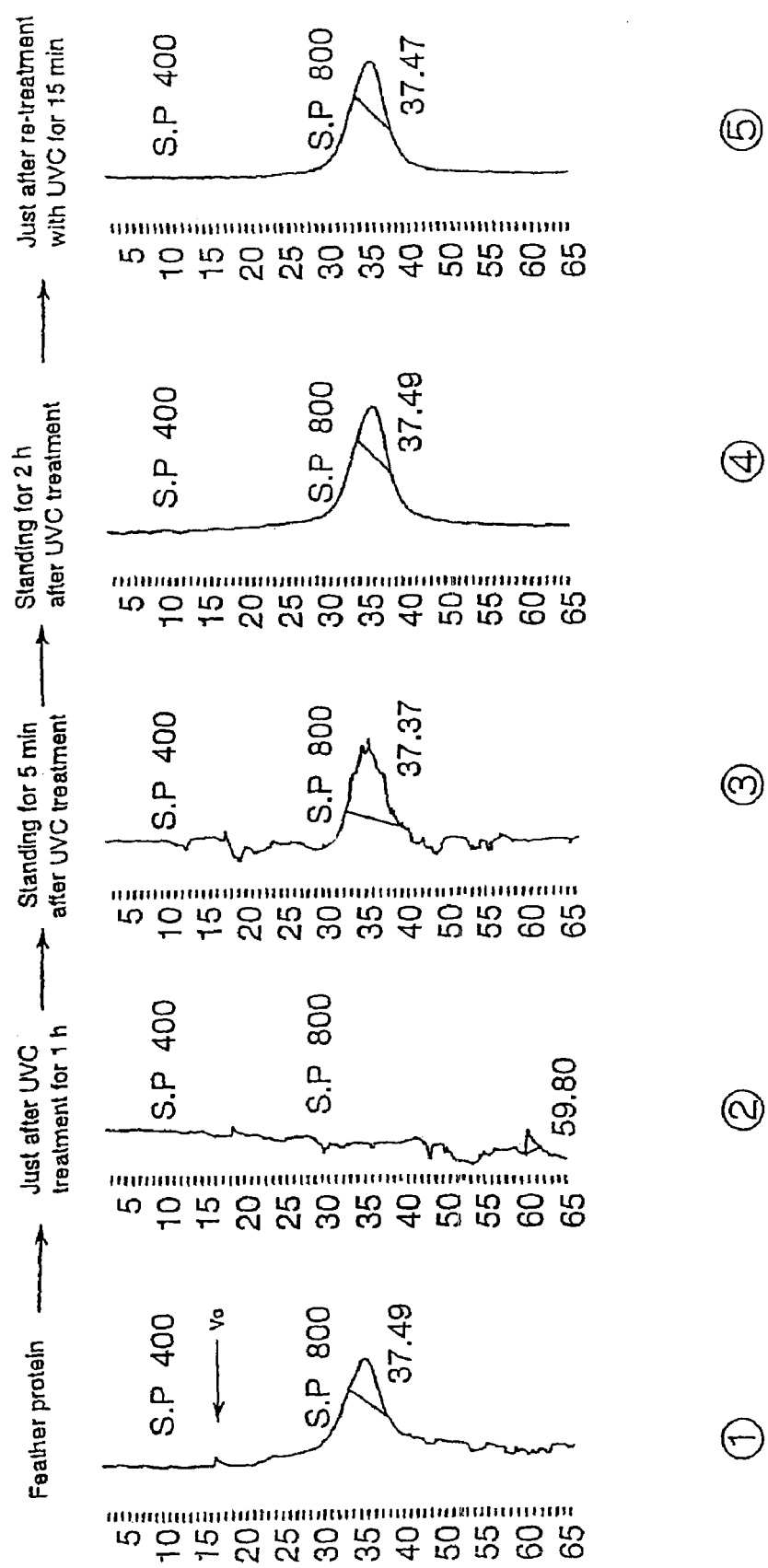
FIG. 14 shows UV-C irradiation response.

HPLC Conditions
Main apparatus: Hitachi HPLC System:
  Pump: L-6200
  Detector: UV-VIS L-4250
Column: Superdex 200 HR 10/30 (Pharmacia)
Measurement Conditions:
  Flow rate: 0.5 mL/min
  Pressure: 7 kg/cm$^2$
  Eluant: PBS (+)
  Absorption wavelength: 280 nm
  Amount added: 5 µL (=5 µg) of 0.1% aqueous solution of MFP
  Temperature: room temperature (9) UV Irradiation Response
a) UV-C Irradiation Response 1 mL of a 0.1% MFP aqueous solution was placed in a quartz cell, irradiated for 1 hour with UV-C at room temperature and 60 µW/cm$^2$, and immediately subjected to HPLC (in which the measurement conditions were the same as above). As shown in section 2 of the chart of FIG. 14, the main peak has been completely eradicated from the spectrum, which is totally different from the case of the untreated MFP shown in section 1. However, the spectrum after 5 minutes of standing (section 3) exhibits a somewhat disturbed pattern, and the spectrum after another 2 hours of standing (section 4) has been completely restored, and there is no change whatsoever in this spectrum after UV-C irradiation under the same conditions for another 15 hours.

These results suggest that UVP, which is like an isomer of MFP, has UV-C irradiation resistance.

b) UV Irradiation Response
0.25% (w/v) UVP was irradiated with UV-A, -B, and -C, and the fluorescence spectra thereof were measured.

Figure 15A:
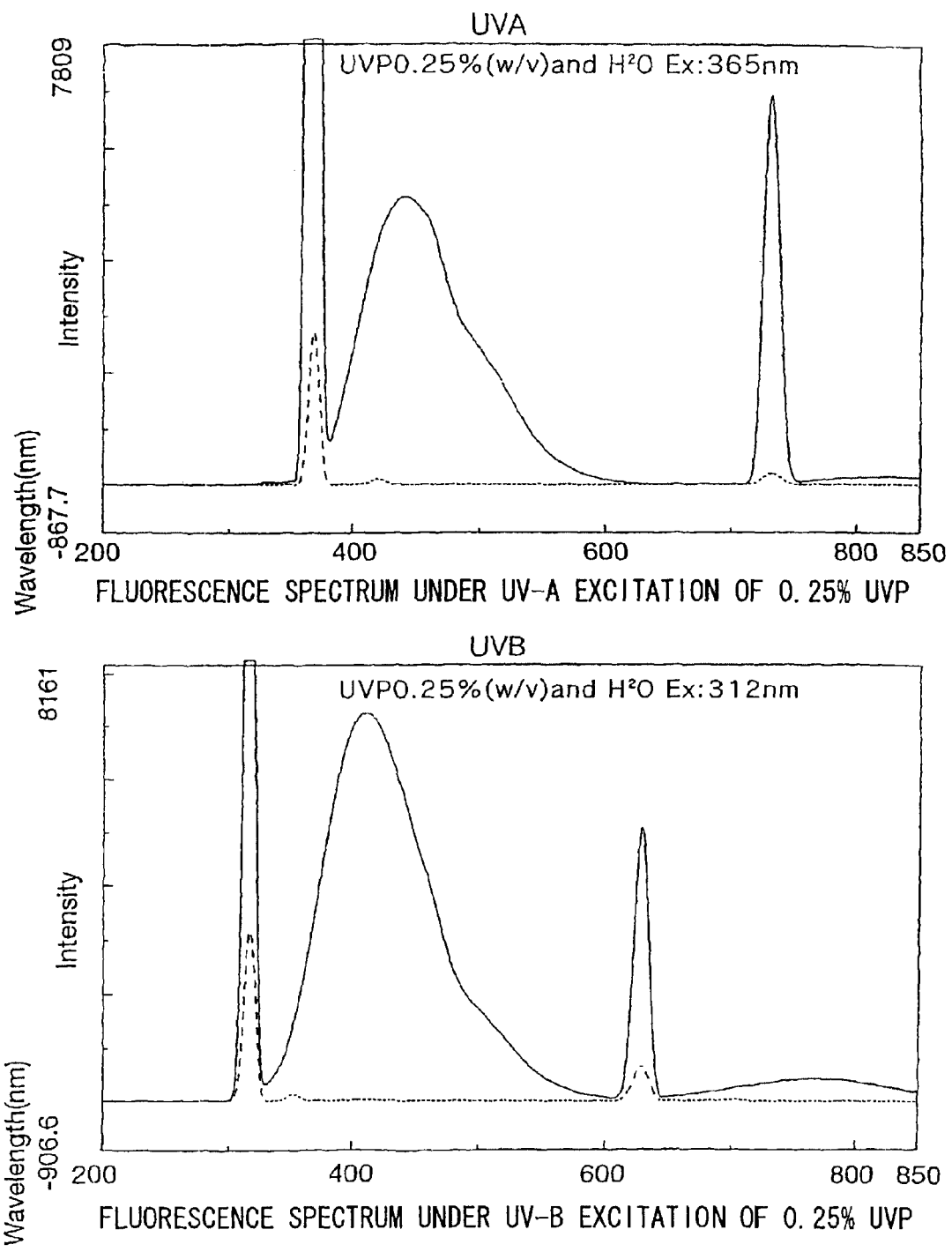
FIGS. 15a and 15b show ultraviolet irradiation response.
Figure 15B:
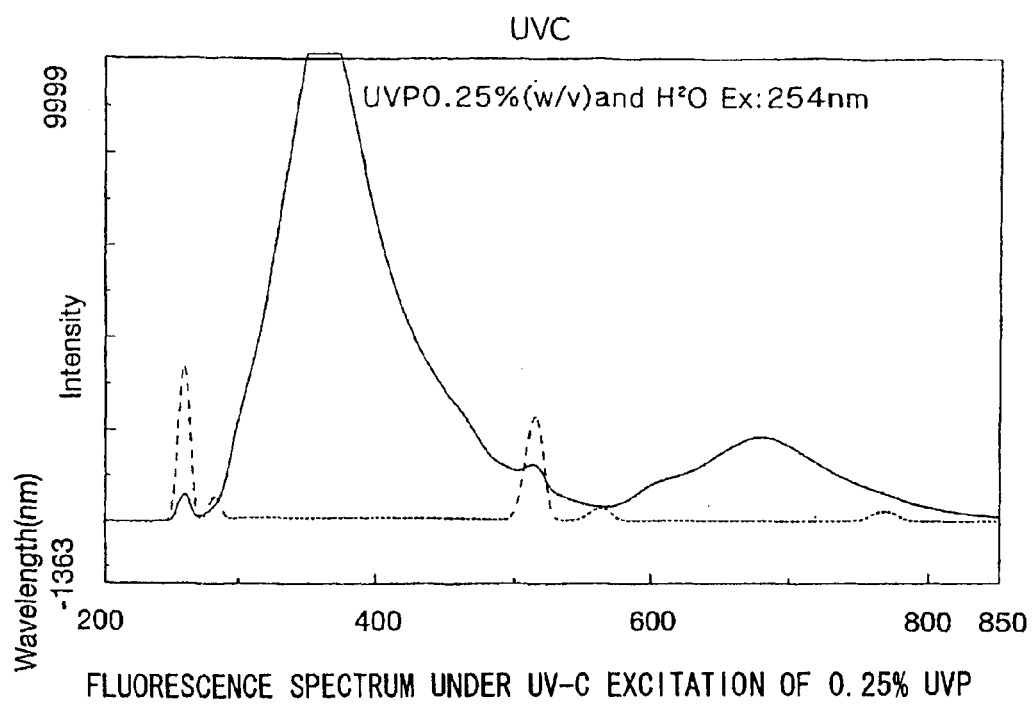

These results are shown in FIG. 15. Under irradiation with UV-A, emission was observed at 450 nm (maximum) and 750 nm (strong), with UV-B at 410 nm (maximum) and 640 nm (medium), and with UV-C at 370 nm (maximum) and 680 nm (medium).

These results indicate that UV rays excite UVP and induce photoluminescence.

(10) Electron Beam Irradiation Response

An electron microscope (SEM) made by JEOL was used for electron beam irradiation, and for spectral measurement, a photon detection system and a spectroscope were installed on this microscope to create a cathode luminescence measurement system.

UVP powder was fixed with adhesive tape to a sample stage, the stage was placed on a stage holder, vacuum evacuation was then performed for 1 hour, the detector was cooled to −30° C., and the sample was irradiated with a 2.0 kV electron beam. Spectral measurement was performed with the irradiating electron beam set to −0.4 nA. This spectrum is shown in FIG. 9.

These results indicate that an electron beam excites UVP and induces photoluminescence.

<Considerations Relating to the Correlation Between Structural Conversion Between MFP and UVP and the Expression of the Characteristics Thereof>

Figure 16:
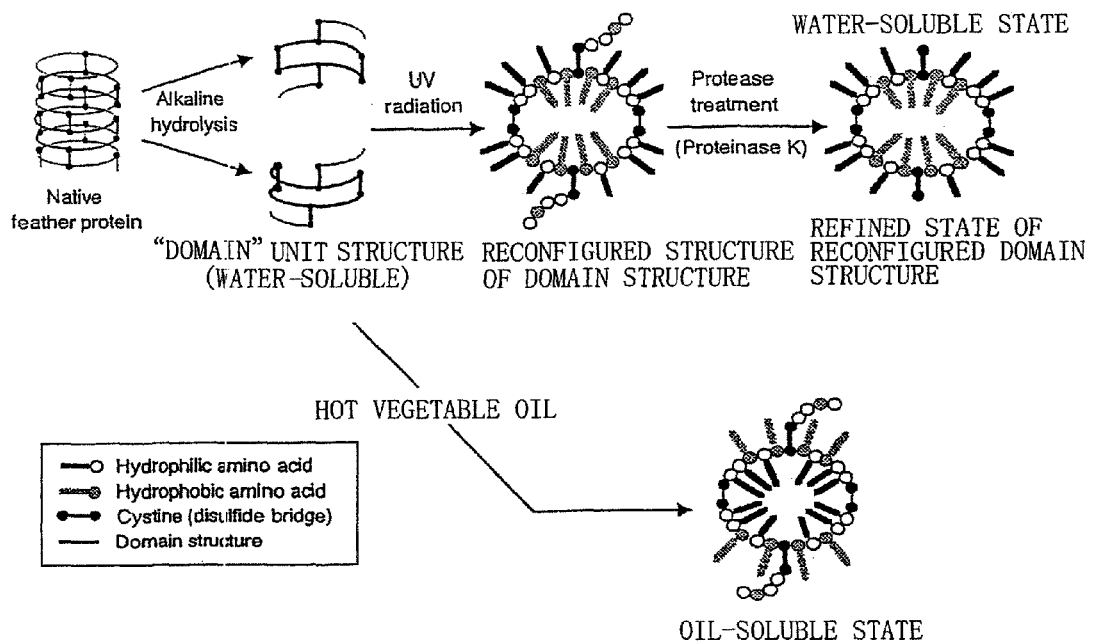
FIG. 16 is a diagram of the correlation between structural conversion between MFP and UVP and the expression of the characteristics thereof.

Details of this are illustrated schematically in FIG. 16. Because the raw material feathers have as their basic structural element a super-lattice (triple chain) structure of multi-point crosslinking (with a high content of cystine residues), we can conclude that MFP comprises a heteropolycyclic peptide structure (simplified as a single ring in the drawings). It is a well known fact that an ionophore of a natural cyclic peptide behaves amphipatically, and it has been reported in recent years that synthetic cyclic peptides are amphipatic, protease resistant, and hydrolysis resistant.

Raw material feathers are readily water-solubilized with an alkali (hydrolysis of peptide bonds) and converted into a water-soluble keratin derivative of several dozen kDa to produce MFP, but once MFP is produced, strong alkali hydrolysis resistance is exhibited. This suggests that MFP is a kind of functional domain, and probably will not decompose any further.

UVP is produced by inducing a UV-C specific irreversible structural conversion by irradiation therewith, and once UVP is produced, the fluorescent emission that is a characteristic excitation moderating action thereof moderates the high energy received upon emission of visible light, and resistance is exhibited not only to UV-C irradiation, but also to the more powerful electron beam irradiation.

This function expression structure center-domain that includes feathers estimated at 10 to 20 kDa might be called a natural, elaborate mechanism that truly allows "two birds with one stone": a bird's ability to fly at super-high altitudes/defense against extremely harsh conditions, and absorption of energy necessary to the preservation of life from said high energy.

Example 3

Water Repellency Test

A microslide glass (made of crown glass) was immersed for 2 minutes in a 1% aqueous solution of each of MFP, the cut low-molecular weight fraction thereof (the filtrate that passed through the UK-10 filter in section 2-4 in Example 1), and UVP, after which each was dried at either room temperature or 50° C. Each product was then brushed and rinsed with tap water, or not, to create two sample groups. Four kinds of specimen plate were prepared for each sample.

Ion exchange water was dropped onto the specimen plate surface, and the contact angle of the water droplets thus formed was measured with a CA-DT contact angle gauge made by Kyowa Interface Science. These results are shown in Table 6.

The contact angle on a control plate was 11 to 14°, whereas the contact angle in the specimen plate group consisting of MFP- and UVP-coated glass that had been brushed and rinsed with tap water was within the range of 23 to 35°, and was therefore clearly significantly larger, which tells us that MFP and UVP both exhibit water repellency.

Meanwhile, the contact angle of the corresponding unwashed specimen plate group was equal to or less than that of the control plate, and a hydrophilic effect was actually exhibited. In the washed and unwashed specimen plate groups comprising glass coated with the cut low-molecular weight fraction (low-molecular weight product), all the specimens exhibited a hydrophilic effect, and it was clear that a high molecular weight is necessary for a water repellency effect to appear.

TABLE 6

| Test No. | Solution used | Drying temperature | Washing performed? | Contact angle (units: °) | | |
|---|---|---|---|---|---|---|
| 1 | untreated | | | 11 | 12 | 14 |
| 2 | MFP | normal temp. | no | 9 | 11 | 11 |
| 3 | | 50° C. | no | 14 | 12 | 12 |
| 4 | | 50° C. | yes | 29 | 35 | 34 |
| 5 | UVP | normal temp. | yes | 25 | 34 | 34 |
| 6 | | normal temp. | no | 12 | 6 | 6 |
| 7 | | 50° C. | yes | 32 | 26 | 26 |
| 8 | | 50° C. | no | 12 | 12 | 7 |
| 9 | low-molecular | normal temp. | no | 9 | 5 | 6 |
| 10 | weight: product | 50° C. | no | 4 | 3 | 4 |
| 11 | | 50° C. | yes | 12 | 14 | 14 |

Example 4

Material Weatherproofness Improvement Test 0.05 part of a commercially available phenol-based antioxidant, 0.05 part of a commercially available phosphorus-based antioxidant, and 0.05 part of a commercially available metallic soap were added to 100 parts general purpose polypropylene to produce a control (testpiece A). This was made into a paste, to which was added 0.15 part MFP (testpiece B), 0.05 part UVP (testpiece C), 0.15 part UVP (testpiece D), or 0.15 part of a commercially available UV absorbent (as a positive control; testpiece E). Each of these samples was pelletized in a processing granulator and then molded into a sheet with a thickness of 2 mm in an injection molding machine to produce testpieces.

Each testpiece was placed in an accelerated weather resistance tester (Sunshine Super-Long-Life Weather-meter made by Suga Test Instruments), and a weather resistance test was conducted for two thousand hours. These results are given in Table 7. The sheets containing MFP and UVP with a commercially available UV absorbent all had markedly less coloration than the control, and a pronounced improvement in weatherproofness was noted. In particular, with the sample to which 0.15 part UVP was added, no surface degradation whatsoever was noted, and the surface remained the same as before the start of the test.

TABLE 7

| Compounding | Testpiece | | | | |
|---|---|---|---|---|---|
| substrate | A | B | C | D | E |
| No addition | 0 | | | | |
| MFP | | 0.15 | | | |
| UVP | | | 0.05 | | |
| UVP | | | | 0.15 | |
| Commercial product | | | | | 0.15 |
| Initial yellow index (Y.I.) | 3.56 | 12.05 | 6.33 | 13.12 | 4.55 |
| Yellow index (Y.I.) after 2000 hours | 20.15 | 13.22 | 7.85 | 14.02 | 10.43 |
| Appearance | cracking | small cracking | cracking | no change | small cracking |

Example 5

Evaluation Test of UV Absorbents

The results of the present invention have clarified that MFP and UVP have the following distinctive characteristics, and these can be deemed to have a high effect versus cost, something not seen in conventional UV absorbents.

- Can absorb the entire bandwidth of UV-A, UV-B, and UV-C.
- Have an absorbed energy moderating action through fluorescent emission, and can be used alone, without any need for auxiliaries.
- Have good sustained absorption and irradiation resistance.
- Have good thermal stability.
- Have high chemical stability.
- Have good hydrolysis resistance.
- Are stable with respect to high energy wave irradiation such as UV-C or an electron beam
- Offer advantages not available in existing products, such as having high water-solubility and being colorless, transparent, and lipophilic.
- Have the following characteristics as a UV absorbent aimed at UV protection.
  - Embryologically, skin and feathers have the same properties, and there is good affinity with skin and hair.
  - Because MFP and UVP are amphipatic, they go smoothly on the skin and hair, making them extremely easy to formulate.
  - MFP and UVP are protein derivatives derived from biological tissue, and are therefore safe and reassuring to the user.
- The raw material recycles resources.
- The raw material is re-produced, so supply stability is high.

Example 6

Foamability Test

The foaming performance of an MFP aqueous solution was measured according to the Ross & Miles method in the Surfactant Handbook (Sangyo Tosho), pp. 858-859, section 7.4.1. Nonylphenol 10 ethoxylate (commercially available product) was used as a control.

TABLE 8

| Measurement conditions | | | Foamability (amount of bubbles mm) | |
|---|---|---|---|---|
| Concentration (%) | Temperature | Sample | Immediately afterward | 5 minutes later |
| 0.1 | room temp. | MFP | 98 | 73 |
| | | control | 123 | 55 |
| 0.2 | room temp. | MFP | 167 | 134 |
| | | control | 160 | 69 |

MFP is on a par with existing products in terms of foaming, but its bubble stability is superior.

INDUSTRIAL APPLICABILITY

The present invention provides a UV absorbent for use in anti-UV skin care products, hair care products, and foundation cosmetics, and a UV absorbent intended as a laundry auxiliary, which are in the form of a single water-soluble agent that has a wide absorption wavelength band, is safe and long-lasting, and has good affinity with skin and hair. The present invention also provides a single-agent weatherproofness improver for synthetic resins and other such organic materials, which is based on a natural protein, is not harmful to ecosystems, and has a high effect versus cost ratio. The present invention further provides a novel organic light emitting material that takes advantage of a function whereby the material emits fluorescent light when irradiated with high energy wave irradiation such as UV-C or an electron beam.

The water-soluble keratin derivative of the present invention is useful as a base for a foaming agent, or as a novel water repellant that is completely water-based and is therefore very safe and environment-friendly.

The invention claimed is:

1. A process for preparing a water-soluble keratin derivative comprising processing of poultry feathers by the following:
   (a) contacting the poultry feathers with an alkali both to desulfurize and to solubilize the feathers in water, thereby forming a water-soluble component and a water-insoluble component;
   (b) separating the water-soluble component from the water-insoluble component by ultra-filtration to obtain a first water-soluble derivative with molecular weight of 10,000 to 50,000 (water-soluble keratin derivative I or MFP), and
   (c) irradiating the MFP with UV-C to obtain a second water-soluble derivative (water-soluble keratin derivative II or UVP) having increased lanthionines and decreased cysteines compared with MFP.

2. The process according to claim 1, wherein the alkali has a concentration of at least 1.1% and the amount of the feathers is at least 2 wt %.

3. The process according to claim 1, wherein the alkali is water-soluable.

4. The process according to claim 3, wherein the water-soluable alkali is caustic soda.

5. The process according to claim 1, wherein the alkali is water-insoluble.

6. The process according to claim 5, wherein the water-soluable insoluble alkali is calcium hydroxide, active clay, or an ion exchange resin.

7. The process according to claim 1, wherein the alkali has a concentration of 4 to 15 wt %.

8. The process according to claim 1, wherein the alkali has a concentration of 4 to 10 wt %.

9. The process according to claim 1, wherein treating the poultry feathers with an alkali is carried out at a temperature of 80° C. or lower.

10. The process according to claim 9, wherein the temperature is from 20° C. to 70° C.

11. The process according to claim 1, wherein irradiating the MFP with UV-C is carried out on an aqueous solution of MFP at a concentration of 1 to 20%.

12. The process according to claim 11, wherein the concentration of MFP is 2 to 10%.

13. The process according to claim 1, wherein irradiating the MFP with UV-C is carried out for 2 to 100 hours at a temperature 80° C. or lower.

* * * * *